US00PP13881P39

(12) United States Plant Patent
Watson

(10) Patent No.: US PP13,881 P3
(45) Date of Patent: Jun. 17, 2003

(54) PLUM TREE NAMED 'JAYFREE PLUM'

(75) Inventor: John P. Watson, deceased, late of Geneva, NY (US), by Judith Watson, executrix

(73) Assignee: Cornell Research Foundation, Inc, Ithaha, NY (US)

( * ) Notice: Subject to any disclaimer, the term of this patent is extended or adjusted under 35 U.S.C. 154(b) by 0 days.

(21) Appl. No.: 09/894,312

(22) Filed: Jun. 27, 2001

(65) Prior Publication Data

US 2003/0005498 P1 Jan. 2, 2003

(51) Int. Cl.[7] ..... A01H 5/00

(52) U.S. Cl. ..... Plt./185

(58) Field of Search ..... Plt./185, 184

*Primary Examiner*—Bruce R. Campell
*Assistant Examiner*—June Hwu

(57) ABSTRACT

A new a distinct variety of prune plum tree, *Prunus domestica,* originating as a hybrid seedling of the cross: 'Valor' (non-patented)×'Iroquois'(non-patented). This new variety is unique from its parents and other prune plums because it is has a freestone, non-shattering stone and flesh which processes very well yielding highly colored, high quality plum products.

6 Drawing Sheets

FIELD OF THE INVENTION

A new and distinct variety of European-type plum tree originated as a seedling of *Prunus domestica* in the breeding program of Cornell University and is hereinafter referred to as 'Jayfree Plum'. This new variety is unique because the fruit has several traits that make it favorable for processing uses (free stone, non-shattering stone, high color retention of processed fruit products and low acidity level of fruit at commercial picking stage for processing uses).

SUMMARY OF THE INVENTION

This new and distinct variety of European plum was discovered in 1975 by John P. Watson (deceased), a plant breeder at the New York State Agricultural Experiment Station, Geneva, N.Y., a research unit of Cornell University, hereinafter referred to as Geneva Experiment Station. By breeding methodology convention at the Geneva Experiment Station it was designated as NY 66.609.6 because it belonged to the Geneva Experiment Station Breeding Record Number 66.609, a hybrid population of trees that resulted from hybridizing the varieties 'Valor' (non-patented)×'Iroquois' (non-patented), and this seedling was the sixth seedling chosen for further evaluation from in a population of ninety-one siblings possessing the same parentage. The orchard location where the seedling was grown and first noticed was designated as Crittenden Farm Field Number 30, Row 7, Tree 194. This seedling was first noticed because it had fruit that was similar to 'Valor' (non-patented) in favorable fruit size but earlier in ripening time. In 1975, buds were taken from the original tree and trees for further testing were asexually reproduced by T-budding and chip budding techniques by Hilltop Nursery LLC, Hartford, Mich. 49057. This new cultivar has been reproduced on plum and peach seedling rootstocks and remains true to the description herein contained.

BRIEF DESCRIPTION OF THE DRAWINGS

The accompanying photographs show typical specimens of the new variety as depicted in color as nearly true as is reasonably possible in color illustrations of this character. These specimens were obtained at the Geneva Experiment Station, Geneva, N.Y.

BOTANICAL DESCRIPTION OF THE PLANT

Figure 1:
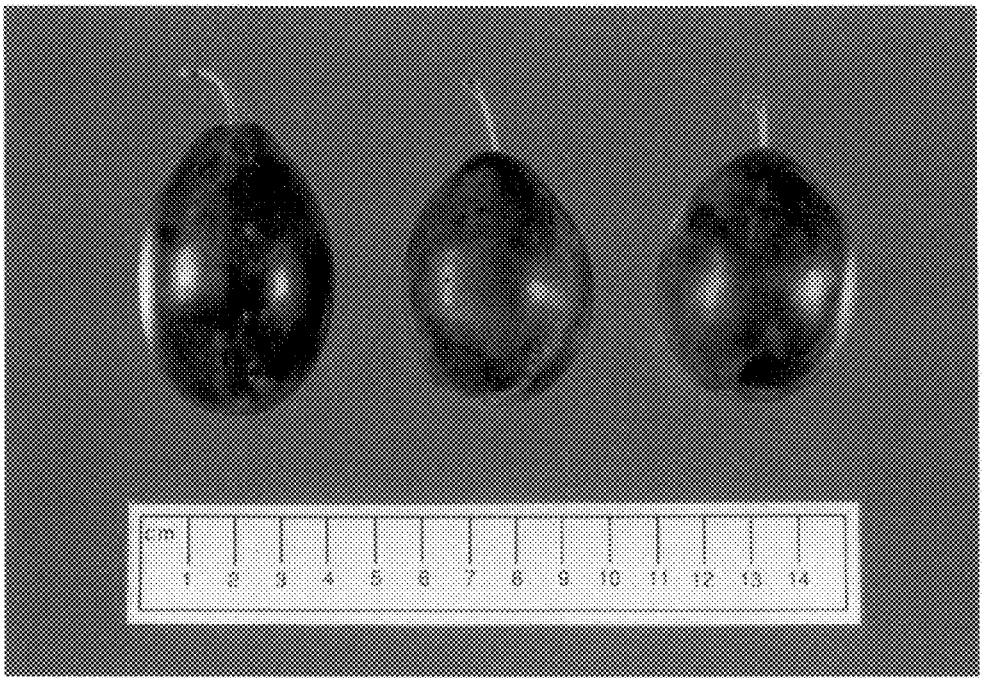
FIG. 1. illustrates the intact fruit of the new variety at maturity.
Figure 2:
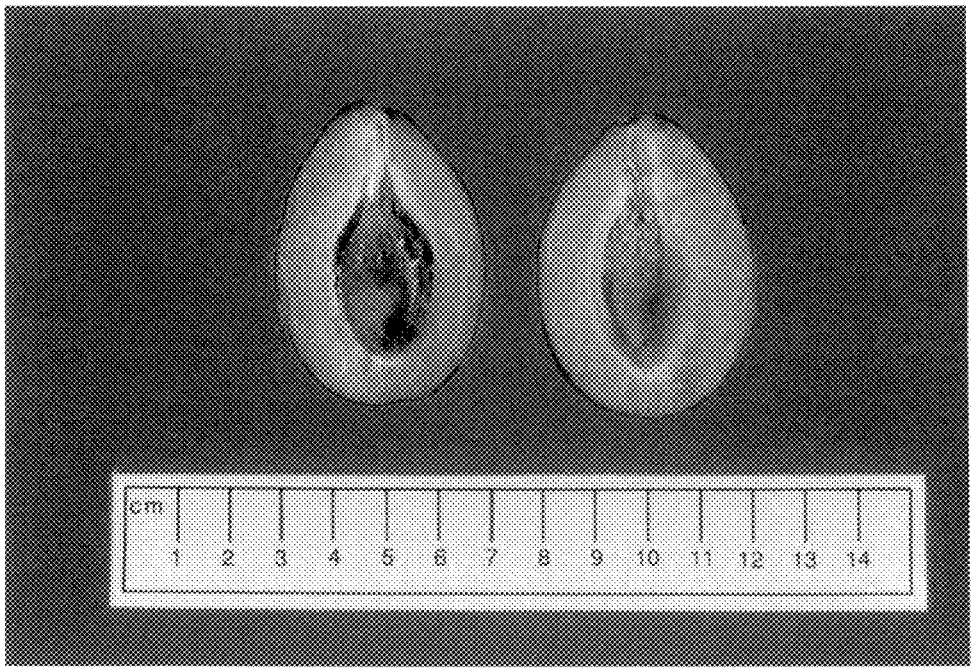
FIG. 2. illustrates the fruit halves of the new variety as cut at the suture line.
Figure 3:
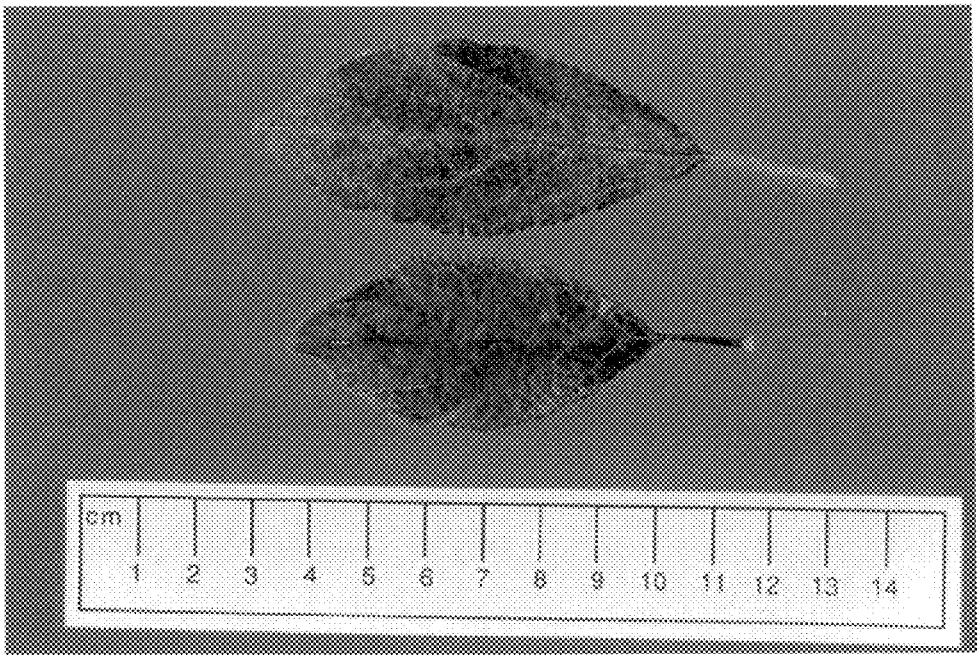
FIG. 3. illustrates the adaxial surface of two leaves of the new variety.
Figure 4:
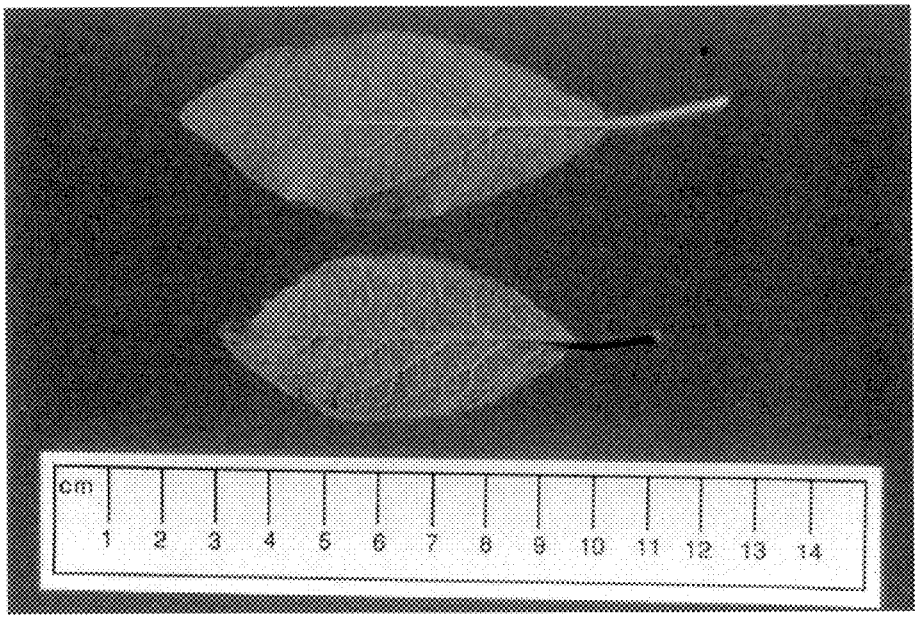
FIG. 4. illustrates the abaxial surface of two leaves of the new variety.
Figure 5:
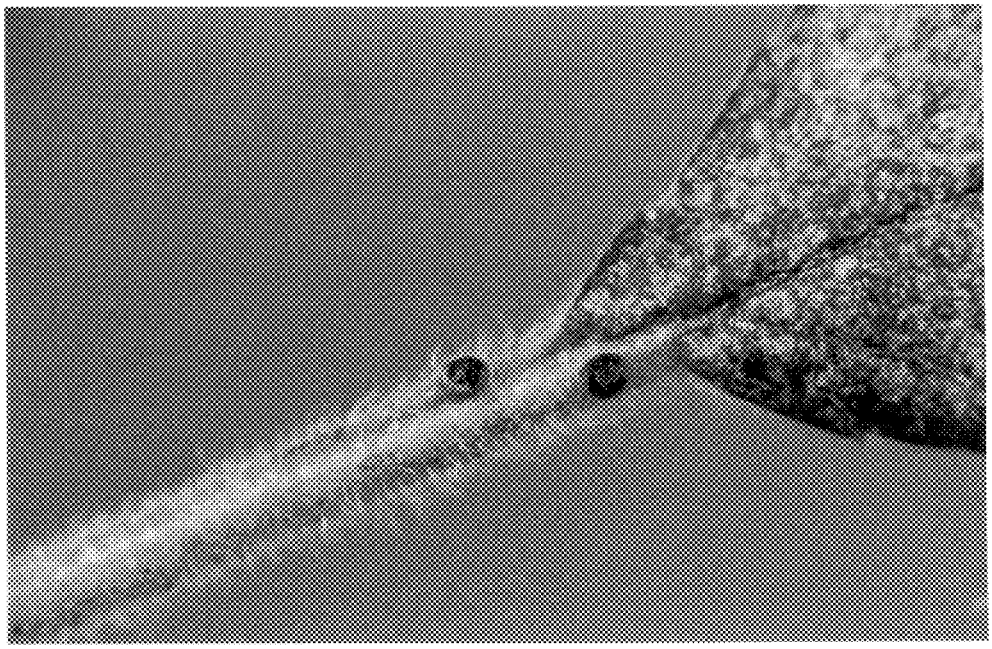
FIG. 5. illustrates a close-up view of leaf petiole and gland at base of leaf blade.
Figure 6:
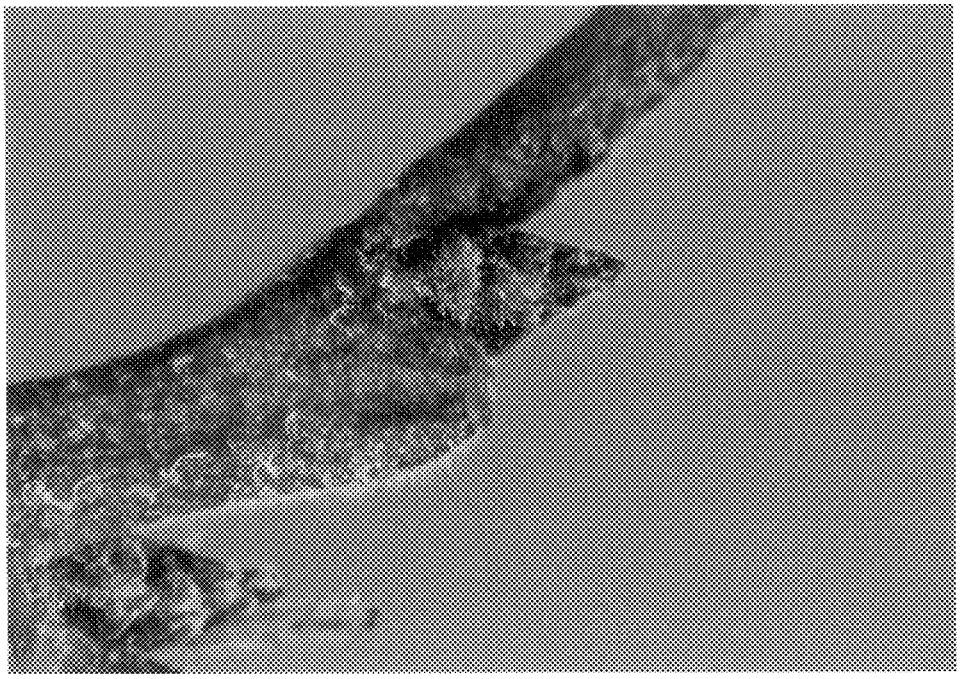
FIG. 6. illustrates vegetative buds of the new variety in close-up.

A detailed description of the 'Jayfree Plum' follows using The Royal Horticultural Society of London Colour Chart for color identification except where general color terms are sufficient.

Parentage: A hybrid seedling of the cross: 'Valor' (non-patented)×'Iroquois' (non-patented).

Locality of the original discovery and observations is the Crittenden Farm Research Orchard Number 30, Row 7, tree 194, Geneva Experiment Station, Geneva, N.Y., U.S.A.

Tree:

*Age of specimen.*—34 years old.
*Height.*—3.5 M.
*Width.*—5 M.
*Size.*—Medium.
*Vigor.*—Medium.
*Density.*—Medium.
*Form.*—Spreading, with high level of lateral branching.

Production: Heavy, with a strong tendency to over-crop and have low flavor and low sugar level in fruits if cultural practices are not imposed to moderate this high crop load tendency.

Bearing: Annual on spurs and one year old shoots.

Disease resistance: More tolerant to black knot fungus of the wood than 'Stanley' (non-patented) but less so than 'NY 58.900.9'; similar to 'Stanley' (non-patented) in tolerance level to brown rot of the blossoms and fruit; immune to Prune Leafcasting Mottle which is a serious physiological disorder of the 'Italian Prune' (non-patented) and most of its progeny.

Insect resistance: More susceptible to attack of European red mite than 'Stanley' (non-patented) and 'Kenmore Plum' (application Ser. No. 09/894,309).

Cold hardiness: Good, crops regularly in test orchards in commercial fruit districts of New York and Michigan.

Graft compatibility: Good, produces compatible graft unions with Mariana 2624, GF 8-1 Mariana, Myrobolan Seedling and Peach Seedling rootstocks.

Trunk:

*Size.*—35 cm in diameter at 60 cm above ground level.

*Surface.*—New bark is smooth with prominent lenticels, older bark remains smooth except for lenticels to ten years or more of age.

*Lenticels.*—Medium in number, varying in length from 1.5 to 8.0 mm and width from 0.5 to 4.0 mm, prominent, horizontal, elliptical, Grayed White 157A perimeters with Grayed Yellow 161B centers.

*Color.*—Older bark, Grey Group 201C where directly exposed to the sun, newer bark Brown Group 200 D.

Vegetative buds:

*Placement.*—At base of leaves on annual growth and at tips of fruiting spurs.

*Appearance.*—Pointed and surrounding bark is pubescent.

*Buds size.*—Length 5 mm, width 2.5 mm at base.

*Spur.*—Pointed apical buds at tips of spurs.

*Bud color.*—Grayed Purple 187 A.

Leaves:

*Size.*—8.0 to 8.5 cm in length, to 3.0 to 6 cm in width with petiole 2.25 to 3.0 cm in length and 2 mm in width.

*Form.*—Elliptic.

*Thickness.*—Medium.

*Texture.*—Crisp.

*Margin.*—Serrated with variable numbers of forward pointing serration-lobes that number from 3 to 4 per 1 cm.

*Adaxial surface.*—Smooth, but not shiny, Green Group 135 B.

*Abaxial surface.*—Dull luster to green coloration, Yellow Green Group 146 B.

*Glands.*—Small, round, often 2 or 3 on leaf petiole near base of leaf blade but usually not integrated into leaf blade tissue.

*Gland color.*—Gray Purple 187 A.

*Average internode length.*—4.5 cm.

*Stipules.*—None observed.

Petiole:

*Surface texture.*—Pubescent.

*Petiole length.*—15 to 20 mm.

*Diameter.*—2.5 mm.

*Petiole color.*—Green 137 A, with some Red Purple 60 A on abaxial surface.

Flowers:

*Blooming period.*—Mid season, May 1 in Geneva, N.Y.

*Bloom duration.*—5 to 9 days.

*Presentation.*—Non showy.

*Fertility.*—Self-fertile.

*Pollen.*—Present.

*Fragrance.*—Faint.

*Corolla diameter.*—14 mm.

*Number of flowers per cluster.*—1 to 3.

*Petals.*—Single, 5 in number, overlapping, round, length 7 mm, length 5 mm, margin very slightly wavy, soft texture, White 155 C.

*Peduncle.*—1.8 to 2.25 cm. in length and 1.75 to 3 mm in width.

*Peduncle color.*—Green 143B.

*Peduncle texture.*—Very slightly pubescent.

*Stamen number.*—18 to 24.

*Filaments.*—Length 6 to 8 mm, width 4 mm, White 155 D.

*Anthers.*—Held above corolla, profuse pollen, pollen color Yellow Green 13 A.

*Style.*—Length 8 mm, color Green 145D.

*Sepals.*—5 in number, bluntly ovate, Green 143 C.

Fruit:

*Maturity when described.*—Commercial ripeness, soluble solid content is 14 degrees Brix.

*Date of first picking.*—Mid-season ripening, August 27–28 at Geneva, N.Y.

*Size.*—4.75 cm to 6.25 cm in length, 4.25 to 4.75 cm in width.

*Form.*—Roundly elongated.

*Base shape.*—Very bluntly pointed.

*Apex.*—Rounded.

*Stem scar.*—Dry.

*Stem cavity.*—Nonexistent to 2 mm indentation.

*Stem length.*—15 to 18 mm.

*Stem color.*—Green 138 B.

*Stem surface texture.*—Smooth.

*Suture.*—Extends around dorsal surface, smooth, slightly indented from 0.1 to 0.2 mm.

*Ventral surface.*—Smooth.

Skin:

*Thickness.*—Medium.

*Tendency to crack.*—May split on suture adjacent to the stem scar/cavity in high rainfall seasons.

*Bloom.*—Present, heavy, conferring light, blue appearance to unhandled fruit at maturity.

*Color.*—Grayed Purple Group 187A with overtones of Purple 79A.

*Flavor.*—Fruity, sweet plum flavor with aromatic essence present, but prone to bland flavor when overset on the tree.

Flesh:

*Texture.*—Medium firm, juicy, retains firm character of flesh after canning as halves.

*Acidity.*—Medium until sugar level gets to above 12 degrees Brix.

*Flavor.*—Excellent with aromatic essence present, but prone to bland flavor if over-set on the tree.

*Aroma.*—Present, pleasing.

*Fibers.*—Moderate.

*Color.*—Yellow Orange 16 A.

*Coloration in the pit cavity.*—Yellow Green 11D and Yellow 16B with very slight coloration of Red Purple 63 A.

*Eating quality.*—Good for fresh use when mature to 14 degrees Brix if eaten when mature and if cropping level is not excessive; excellent for infant food processed products because it has moderate acidity and essential levels of sugar and aroma levels.

Stone:

*Color.*—Slightly pigmented Red 63 B over Grey Brown 199 C endocarp.

*Size.*—2.5 to 3 cm in length, usually 1.75 to less than 2 cm in width at widest point near the center, 0.5 cm in width at widest point of the flatter direction.

*Form.*—Ovate, asymmetrical, stem end more pointed than apical end with widest point at center or two-thirds distance from stem end.

*Apex.*—Pointed, possessing a slightly prominent tip which has shown no tendency to fracture during processing.

*Sides.*—Very slightly winged on suture.

*Base.*—Usually round but occasionally medium pointed.

*Surface.*—Rough.

*Type.*—Freestone at commercial maturity.

*Tendency to crack.*—Non-existent.

Use: Dual purpose for either fresh market or processed as whole, halves, coarse puree for bakery products, for infant food puree.

It is claimed:

1. A new and distinct variety of European-type plum tree, *Prunus domestica,* substantially as herein shown and described, characterized as to novelty by the unique combination of a free, non-shattering stone, highly colored processed plum products of excellent quality, yielded by a tree that is spreading in habit and precocious in bearing early, large crops of fruit which have acceptable fresh market size and good eating quality and shipping/handling attributes that meet grade standards for this fruit.

* * * * *